(12) United States Patent
Alekshun et al.

(10) Patent No.: US 9,078,811 B2
(45) Date of Patent: Jul. 14, 2015

(54) METHODS OF INCREASING ORAL BIOAVAILABILITY OF TETRACYCLINES

(75) Inventors: Michael N. Alekshun, Marlboro, MA (US); Adel Bakhtyari, Andover, MA (US); Sean Johnston, Doylestown, PA (US); Masha Pukshansky, Brookline, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 1215 days.

(21) Appl. No.: 11/657,412

(22) Filed: Jan. 24, 2007

(65) Prior Publication Data

US 2008/0070873 A1  Mar. 20, 2008

Related U.S. Application Data

(60) Provisional application No. 60/761,819, filed on Jan. 24, 2006.

(51) Int. Cl.
*A61K 31/65* (2006.01)
*A61K 9/00* (2006.01)

(52) U.S. Cl.
CPC .................................. *A61K 9/0019* (2013.01)

(58) Field of Classification Search
USPC ................................................ 514/153, 152
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,062,717 A | 11/1962 | Hammer | |
| 3,165,531 A | 1/1965 | Nelson et al. | |
| 3,454,697 A | 7/1969 | Joyner et al. | |
| 3,557,280 A | 1/1971 | Weber et al. | |
| 3,674,859 A | 7/1972 | Beutel et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 5,277,916 A * | 1/1994 | Dwyer et al. | 424/494 |
| 6,172,084 B1 * | 1/2001 | Cuny et al. | 514/312 |
| 6,475,493 B1 * | 11/2002 | Mulye | 424/400 |
| 6,683,068 B2 | 1/2004 | Nelson et al. | |
| 6,818,635 B2 | 11/2004 | Nelson et al. | |
| 6,841,547 B2 * | 1/2005 | Brown et al. | 514/152 |
| 6,846,939 B2 | 1/2005 | Nelson et al. | |
| 7,008,640 B2 * | 3/2006 | Watanabe et al. | 424/458 |
| 7,056,902 B2 | 6/2006 | Nelson et al. | |
| 2003/0118547 A1 * | 6/2003 | Vandenberg | 424/85.4 |
| 2003/0180352 A1 * | 9/2003 | Patel et al. | 424/465 |
| 2005/0037071 A1 | 2/2005 | Cao et al. | |
| 2005/0038002 A1 | 2/2005 | Nelson et al. | |
| 2005/0137174 A1 | 6/2005 | Ohemeng et al. | |

FOREIGN PATENT DOCUMENTS

| | | |
|---|---|---|
| EP | 0052404 A2 | 5/1982 |
| EP | 0418565 A2 | 3/1991 |
| EP | 0470047 A1 | 2/1992 |
| GB | 2414668 A | 12/2005 |
| JP | 4-159222 A | 6/1992 |
| WO | WO-0204406 A2 | 1/2002 |
| WO | WO-02072031 A2 | 9/2002 |
| WO | WO-03013421 A2 | 2/2003 |
| WO | WO-2004091513 A1 | 12/2003 |
| WO | WO-2004038000 A2 | 5/2004 |
| WO | WO-2005009943 A2 | 2/2005 |
| WO | WO-2005009944 A1 | 2/2005 |
| WO | WO-2005046651 A1 | 5/2005 |

OTHER PUBLICATIONS

Banerjee et al., "The Transport of Tetracyclines Across the Mouse Ileum in-Vitro: the Effect of Cations and Other Agents", *J. Pharm. Pharacol.*, 28(2):133-138 (1976).
Berge et al., "Pharmaceutical Salts", *J. Pharm. Sci.*, 66(1):1-19 (1977).
Hirono et al., "Non-congeneric Structure-Pharmacokinetic Property Correlation Studies Using Fuzzy Adaptive Least-Squares: Oral Bioavailability", *Biol. Pharm. Bull.*, 17(2):306-309 (1994).
Poiger et al., "Interaction of cations and chelators with the intestinal absorption of tetracycline", *Naunyn-Schmiedeberg's Arch. Pharm.*, 306(1):89-92 (1979).
Rogalski, "Chemical modification of the tetracyclines", In Hlavka JJ, Boothe JH, eds. The Tetracyclines. Handbook of Experimental Pharmacology, vol. 78, p. 179-316 (1985). Springer-Verlag Berlin Heidelberg.
Mitsuru Hashida. Keiko toyo seizai no sekkei to hyoka. (1995):198-215.
Richardson et al. "Synthesis and Structure—Activity Relationships of Novel Arylpiperazines as Potent and Selective Agonists of the Melanocortin Subtype-4 Receptor." *J. Med. Chem.* 47(2004):744-755.

* cited by examiner

*Primary Examiner* — Savitha Rao

(74) *Attorney, Agent, or Firm* — McCarter & English, LLP; Elizabeth A. Hanley

(57) ABSTRACT

Methods for increasing the oral bioavailability of tetracycline compounds are described.

12 Claims, No Drawings

METHODS OF INCREASING ORAL BIOAVAILABILITY OF TETRACYCLINES

RELATED APPLICATIONS

This application claims priority to U.S. Provisional Patent Application Ser. No. 60/761,819, filed on Jan. 24, 2006; the entire contents of which are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and Salmonella). The rise of tetracycline-resistant organisms has resulted in a general decline in use of tetracyclines and tetracycline analogue compositions as antibiotics of choice. Methods and compositions for the oral bioavailability of tetracycline compounds would be of great benefit.

SUMMARY OF THE INVENTION

In one embodiment, the invention pertains to methods of increasing the oral bioavailability of a tetracycline compound in a subject. The method includes administering to a subject a tetracycline compound in combination with a bioavailability enhancing agent such that the tetracycline compound is released in the intestinal tract.

In another embodiment, the invention pertains to a pharmaceutical composition comprising a therapeutically effective amount of a tetracycline compound in combination with a bioavailability enhancing agent and a pharmaceutically acceptable carrier for administration of said tetracycline compound to the intestinal tract.

In a further embodiment, the invention pertains to a kit comprising a tetracycline compound and instructions for administering a therapeutically effective amount of the tetracycline compound in combination with a bioavailability enhancing agent to the intestinal tract of a subject.

DETAILED DESCRIPTION OF THE INVENTION

In one embodiment, the invention pertains to methods of increasing the oral bioavailability of a tetracycline compound in a subject. The method includes administering to a subject a tetracycline compound in combination with a bioavailability enhancing agent such that the tetracycline compound is released in the intestinal tract.

The phrase "released in the intestinal tract" refers to the dispersion of the tetracycline in the intestinal tract. The intestinal tract as used herein, includes, for example, the small intestine, the large intestine, the duodenum, the jejunum, the ileum, the colon, and the cecum. Furthermore, the term "the intestinal tract" does not include the mouth, the pharanx, the esophagus, the cardia and the stomach. In one embodiment, the tetracycline compound is released into the small intestine. In another embodiment, the tetracycline compound is released into the duodenum. Methods for releasing the tetracycline compound into the intestinal tract include, for example, the administration of the tetracycline compound in a formulation with an enteric coating, administration by directly injecting the tetracycline compound into the intestinal tract, administration of the tetracycline via a gastric feeding tube and administration of the tetracycline compound by a duodenal feeding tube.

The term "bioavailability" includes, generally, the degree to which a drug or other substance becomes available to a target tissue after administration. In a further embodiment, the bioavailability of the of the tetracycline compounds may be the bioavailability to a particular target tissue. For example, in an embodiment, the particular target tissue may require traversal of the stomach or the small intestines, therefore the bioavailability data may be obtained from this particular target tissue.

The term "target tissue" includes any tissue or body fluid of a subject, preferably human. For example, the target tissue may be the brain, blood, nerves, spinal cord, heart, liver, kidneys, stomach, small intestine, duodenum, muscles, lung, pancreas, intestine, bladder, reproductive organs, bones, tendons, or other internal organs or tissues.

bioavailability can be determined according to the following equation:

$$\% F = (AUC)_{po}/(AUC)_{i.v.} \times (Dose)_{iv}/(Dose)_{po}$$

In this equation, % F is the fraction of the compound absorbed. AUC is the experimentally determined "area under the curve" and is related to other pharmacodynamic parameters such as clearance (CL), volume of distribution ($V_d$), and elimination half-life ($t_{1/2}$) (See Hirono, S. et al. Biol Pharm Bull 1994, 17, 306-309).

The bioavailability of the tetracycline compound may be enhanced by the addition of a bioavailability enhancing agent. The term "bioavailability enhancing agent" includes agents that, when administered in combination with the tetracycline compound, increase the availability of the tetracycline compound to the target tissue. Suitable bioavailability enhancing agents include, for example, charge masking compounds, solubilizing compounds, reducing compounds, stabilizing compounds, lubricating compounds, enteric coatings, permeability enhancing compounds, or combinations thereof. In one embodiment, the bioavailability enhancing agent is, for example, polysorbate 80 (TWEEN-80), ethylenediaminetetraacetic acid (EDTA), sodium bisulfite, octanol, oil, ethanol, calcium chloride, or silicon dioxide. In a further embodiment, the bioavailability enhancing agent is a lubricating agent in combination with another bioavailability enhancing agent. Examples of combinations include sodium bisulfite with a lubricating compound such as AEROSIL 200.

In one embodiment, the bioavailability of the tetracycline compound when administered in combination with the bioavailability enhancing agent is increased by about 5% or greater, by about 10% or greater, by about 25% or greater, by about 40% or greater or by about 50% or greater as compared to the bioavailability of the compound when not specifically administered to the intestinal tract, i.e., orally administered via mouth without an enteric coating.

The language "in combination with" a bioavailability enhancing agent includes co-administration of the tetracycline compound and the bioavailability enhancing agent, administration of the tetracycline compound first, followed by the bioavailability enhancing agent and administration of the bioavailability enhancing agent, followed by the tetracycline compound. The bioavailability enhancing agent and the tetracycline compound may be administered at any interval which allows the compounds to perform their intended function, e.g., increase to oral bioavailability of the tetracycline compound. The bioavailability enhancing agent and the tetracycline compound may be administered concurrently in separate or in the same pharmaceutical composition. In other embodiment, the tetracycline compound and the bioavailability enhancing agent may be administered within about 30 minutes, within about one hour, within about two hours, or within another period of time which allows the compounds to perform their intended function.

The term "subject" includes animals (e.g., mammals, e.g., cats, dogs, horses, pigs, cows, sheep, rodents, rabbits, squirrels, bears, primates (e.g., chimpanzees, gorillas, and humans)). It also includes transgenic animal models.

The term "tetracycline compound" includes substituted or unsubstituted tetracycline compounds or compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

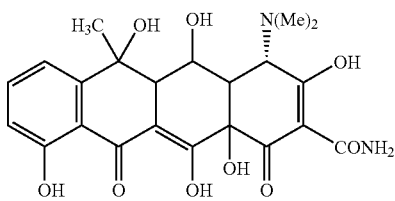

Oxytetracycline

TABLE 1-continued

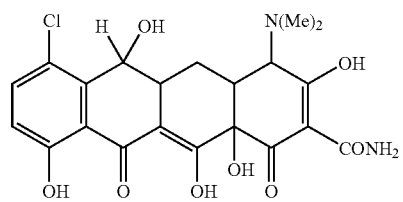

Demeclocycline

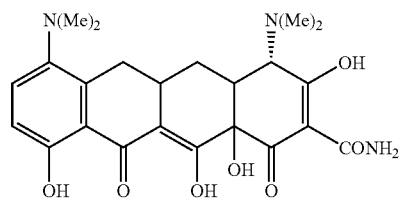

Minocycline

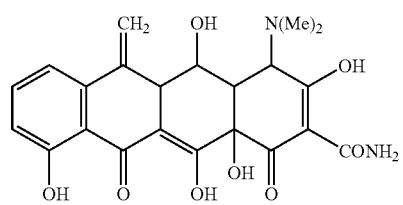

Methacycline

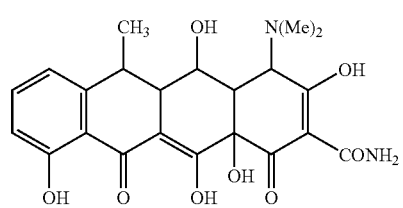

Doxycycline

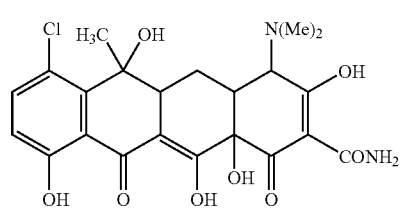

Chlortetracycline

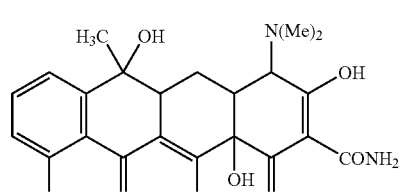

Tetracycline

TABLE 1-continued

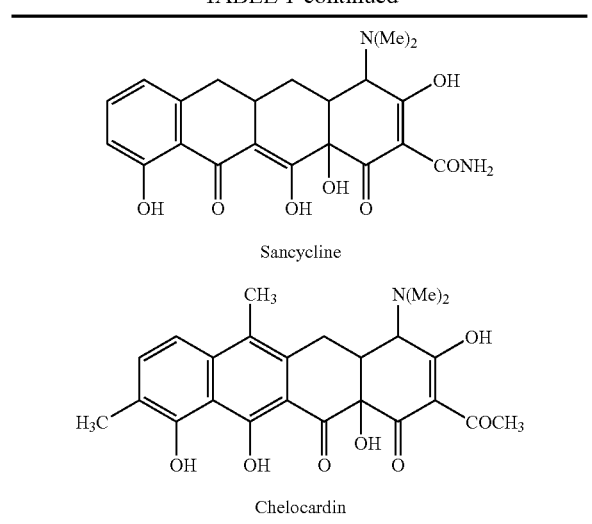

Sancycline

Chelocardin

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a C1-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a,6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a,11a dehydro tetracyclines; 11a C1-6, 12 hemiketal tetracyclines; 11a C1-6-methylene tetracyclines; 6,13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines; 6-αacetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5,12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

The term "substituted tetracycline compound" includes tetracycline compounds with one or more additional substituents, e.g., at the 1, 2, 3, 4, 5, 6, 7, 8, 9, 10, 11, 11a, 12, 12a or 13 position or at any other position which allows the substituted tetracycline compound of the invention to perform its intended function.

In a one embodiment, the tetracycline compound of the invention is of formula I:

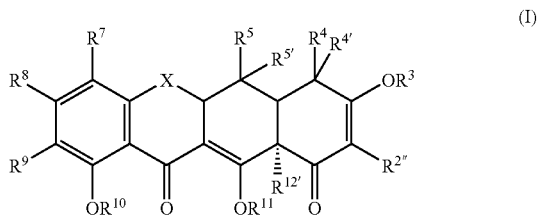

wherein $R^1$ is hydrogen, alkyl, alkenyl, alkynyl, aryl, arylalkyl, amido, alkylamino, amino, arylamino, alkylcarbonyl, arylcarbonyl, alkylaminocarbonyl, alkoxy, alkoxycarbonyl, alkylcarbonyloxy, alkyloxycarbonyloxy, arylcarbonyloxy, aryloxy, thiol, alkylthio, arylthio, alkenyl, heterocyclic, hydroxy, or halogen, optionally linked to $R^2$ to form a ring;

$R^{2''}$ is cyano or $C(=O)-NR^2R^{2'}$;

$R^2$ is hydrogen, alkyl, halogen, alkenyl, alkynyl, aryl, hydroxyl, thiol, cyano, nitro, acyl, formyl, alkoxy, amino, alkylamino, heterocyclic, or absent, optionally linked to $R^1$ to form a ring;

$R^{2'}$, $R^{4a}$, and $R^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{10}$, $R^{11}$, and $R^{12}$ are each independently hydrogen, alkyl, aryl, benzyl, arylalkyl, or a pro-drug moiety;

$R^{12''}$ is $O-R^{12}$, hydrogen, or substituted amino;

$R^4$ and $R^{4'}$ are each independently $NR^{4a}R^{4b}$, alkyl, acyl, alkenyl, alkynyl, hydroxyl, halogen, hydrogen, or taken together $=N-OR^{4a}$;

$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

$R^7$ is hydrogen, dialkylamino, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, boronic ester, alkylcarbonyl, thionitroso, or $-(CH_2)_{0-3}(NR^{7c})_{0-1}C(=W')WR^{7a}$;

$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;

$R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{9c})_{0-1}C(=Z')ZR^{9a}$;

$R^{7a}$, $R^{7b}$, $R^{7c}$, $R^{7d}$, $R^{7e}$, $R^{7f}$, $R^{8a}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{13}$ is hydrogen, hydroxy, alkyl, alkenyl, alkynyl, alkoxy, alkylthio, aryl, alkylsulfinyl, alkylsulfonyl, alkylamino, or an arylalkyl;

E is $CR^{8d}R^{8e}$, S, $NR^{8b}$ or O;

E' is O, $NR^{8f}$ or S;

Q is a double bond when $R^2$ is absent, Q is a single bond when $R^2$ is hydrogen, alkyl, halogen, hydroxyl, thiol, alkenyl, alkynyl, aryl, acyl, formyl, alkoxy, amino, alkylamino, cyano, nitro, or heterocyclic;

W is $CR^{7d}R^{7e}$, S, $NR^{7b}$ or O;

W' is O, $NR^{7f}$, or S;

X is $CHC(R^{13}Y'Y)$, $C=CR^{13}Y$, $CR^{6'}R^6$, S, $NR^6$, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is $CR^{9d}R^{9e}$, S, $NR^{9b}$ or O;

Z' is O, S, or $NR^{9f}$, and pharmaceutically acceptable salts, esters and enantiomers thereof.

In another embodiment, $R^{2''}$ is $C(=O)NH_2$; $R^3$, $R^{10}$, $R^{11}$, and $R^{12}$ are each hydrogen or a prodrug moiety; $R^4$ is $NR^{4a}R^{4b}$; $R^{4a}$ and $R^{4b}$ are each methyl; $R^5$ is hydrogen; $R^8$ is hydrogen; X is $CR^6R^{6'}$; $R^6$ is hydrogen; and $R^{5'}$ and $R^{6'}$ are hydrogen.

In a further embodiment, the tetracycline compound of the invention is of formula II:

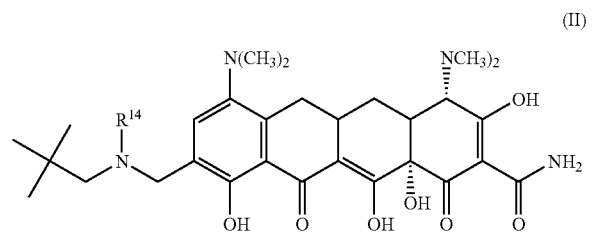

(II)

wherein $R^{14}$ is hydrogen or prodrug moiety, and pharmaceutically acceptable salts thereof.

In one embodiment, $R^{14}$ is hydrogen.

In a further embodiment, $R^{14}$ is of the formula

—(C=O)-$E^1$-$G^1$ wherein $E^1$ is oxygen, nitrogen, or a covalent bond;

$G^1$ is alkyl; heterocyclicalkyl; aryl; alkylcarbonyloxyalkyl; arylcarbonyloxyalkyl; alkyloxycarbonyloxyalkyl; arylalkylcarbonyloxyalkyl; alkyloxyalkylcarbonyloxyalkyl; or alkoxyalkoxycarbonyloxyalkyl.

In one embodiment, $E^1$ is a covalent bond and $G^1$ is alkyl.

In another embodiment, $E^1$ is nitrogen and $G^1$ is aryl, such as substituted or unsubstituted phenyl.

In one embodiment, $E^1$ is oxygen and $G^1$ is alkylcarbonyloxyalkyl. In yet another embodiment, $G^1$ is of the formula —$(CH_2)_m$—O—(C=O)—$R^{15}$, wherein m is 1-5 and $R^{16}$ is alkyl. In a further embodiment, m is 1 or 2. In yet another embodiment, $R^{15}$ is methyl, ethyl, propyl, butyl, pentyl, hexyl, heptyl, octyl, nonyl, decyl, —$(CH_2)_{10}$—$CH_3$, or —$(CH_2)_{11}CH_3$. In a further embodiment, $R^{15}$ is cycloalkyl.

In one embodiment, $E^1$ is oxygen and $G^1$ is —$(CH_2)_2$—O—C(=O)—$CH_3$. In another embodiment, $E^1$ is oxygen and $G^1$ is —$CH_2$—O—(C=O)—$C(CH_3)_3$.

In one embodiment, $E^1$ is oxygen and $G^1$ is alkyl. Suitable alkyl groups include, for example, methyl, ethyl, propyl, butyl, pentyl, hexyl, heptyl, octyl, nonyl, decyl, —$(CH_2)_{10}$—$CH_3$, or —$(CH_2)_{11}CH_3$.

In one embodiment, $E^1$ is oxygen and $G^1$ is arylcarbonyloxyalkyl. In one particular embodiment, $G^1$ is of the formula: —$(CH_2)_f$—O—(C=O)—$R^{17}$, wherein f is 1-5 and $R^{17}$ is aryl. In a further embodiment, f is 1 and $R^{17}$ is substituted or unsubstituted phenyl. Suitable substituted phenyl groups include, for example, phenyl substituted with one or more substituents selected from the group consisting of halogen, alkoxy, or alkyl.

In yet another embodiment, $E^1$ is oxygen and $G^1$ is alkyloxycarbonyloxyalkyl. In one particular embodiment, $G^1$ is of the formula —$(CH_2)$—O—(C=O)—O—$R^{18}$, wherein $R^{18}$ is alkyl. Suitable alkyl groups, include, for example, methyl, ethyl, propyl, butyl or pentyl.

In a further embodiment, $E^1$ is oxygen and $G^1$ is arylalkylcarbonyloxyalkyl. In one particular embodiment, $G^1$ is of the formula —$(CH_2)$—O—(C=O)—$(CH_2)_h$—$R^{19}$, wherein h is 1-5, and $R^{19}$ is aryl. In another embodiment, h is 1 or 2 and $R^{19}$ is phenyl.

In a further embodiment, $E^1$ is oxygen and $G^1$ is alkyloxyalkylcarbonyloxyalkyl. In one particular embodiment, $G_1$ is of the formula —$(CH_2)$—O—(C=O)—$(CH_2)_i$—O—$R^{20}$, wherein i is 1-5, and $R^{20}$ is alkyl. In a further embodiment, i is 1, 2, or 3. In yet another embodiment, $R^{20}$ is methyl.

In one embodiment, $E^1$ is oxygen and $G^1$ is alkoxyalkoxyalkylcarbonyloxyalkyl. In one particular embodiment, $G_1$ is of the formula —$(CH_2)$—O—(C=O)—$(CH_2)_j$—O—$(CH_2)_k$—O—$R^{21}$, wherein j and k are each 1-5, and $R^{21}$ is alkyl. In one embodiment, j is 1 and k is 2. In a further embodiment, $R^{21}$ is methyl.

In yet another embodiment, $E^1$ is oxygen and $G^1$ is heterocyclic alkyl.

In a further embodiment, the tetracycline compound is:

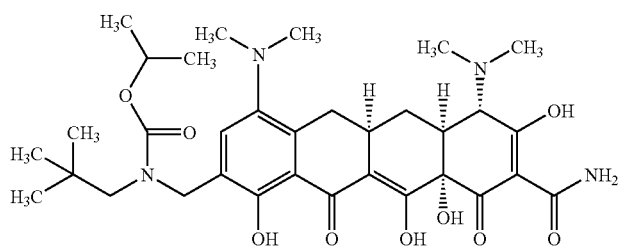

-continued
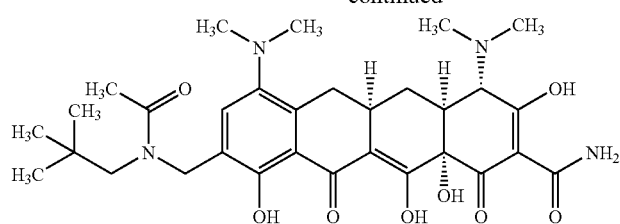
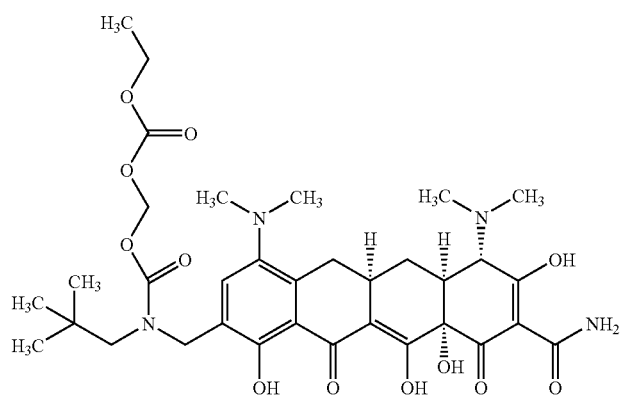
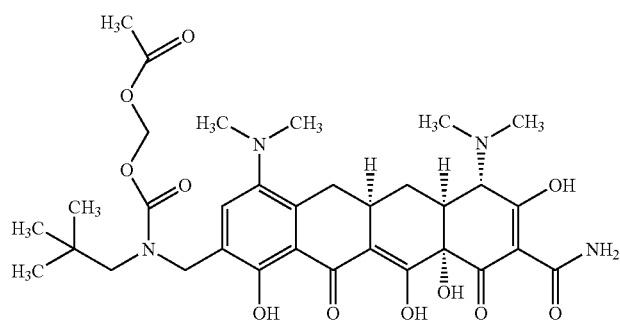
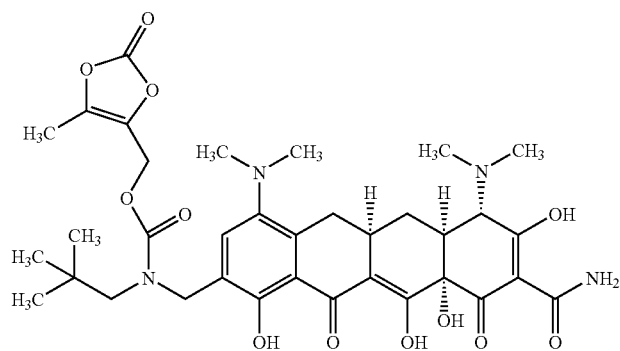

-continued
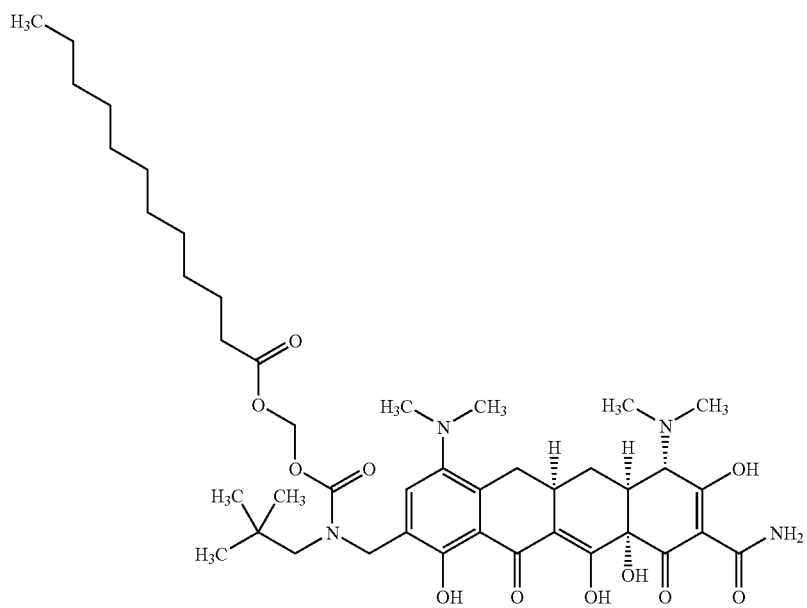
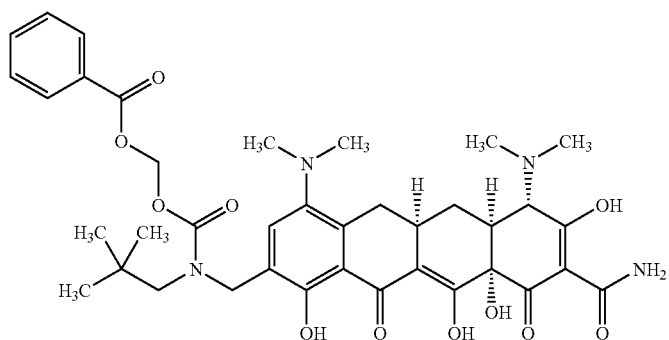
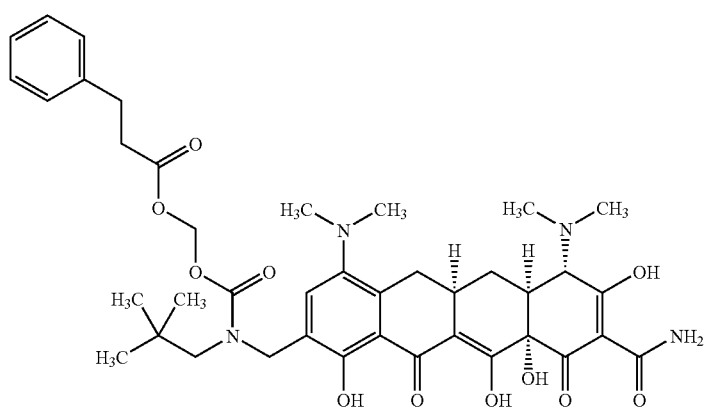
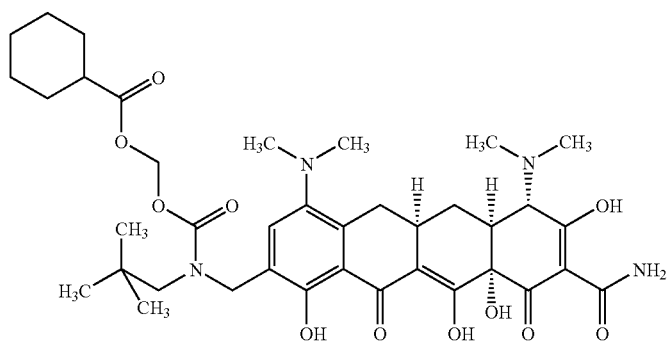

-continued
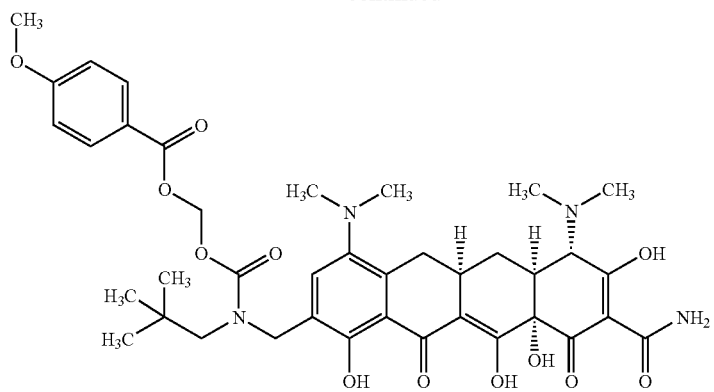
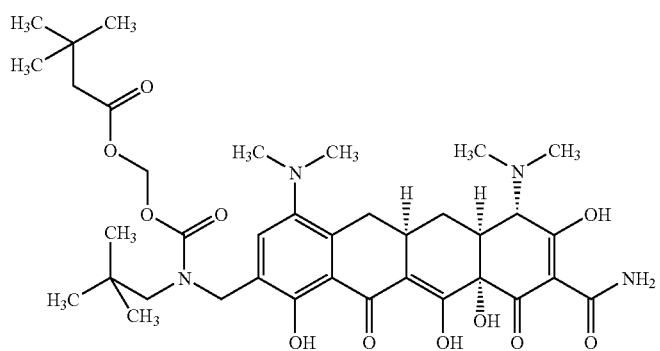
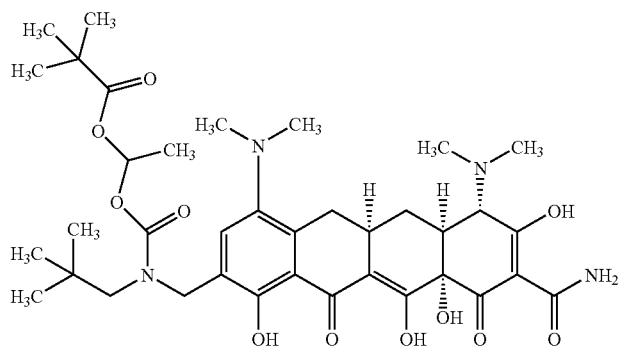
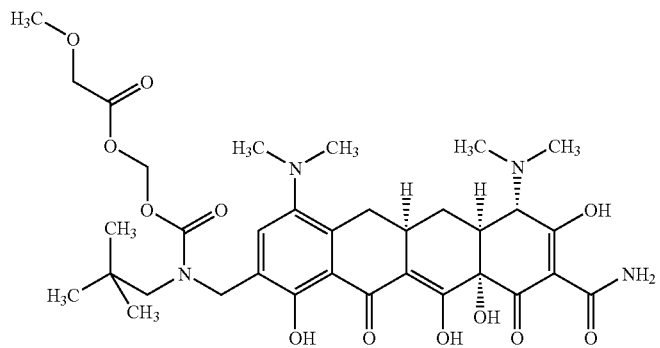

-continued
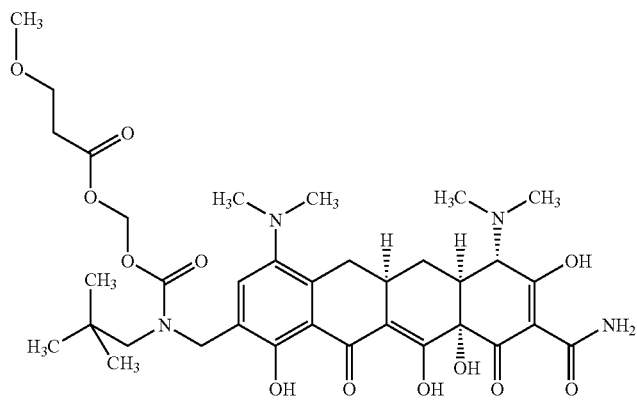
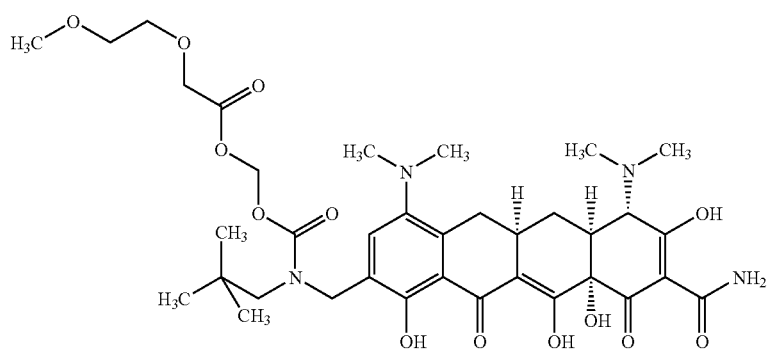
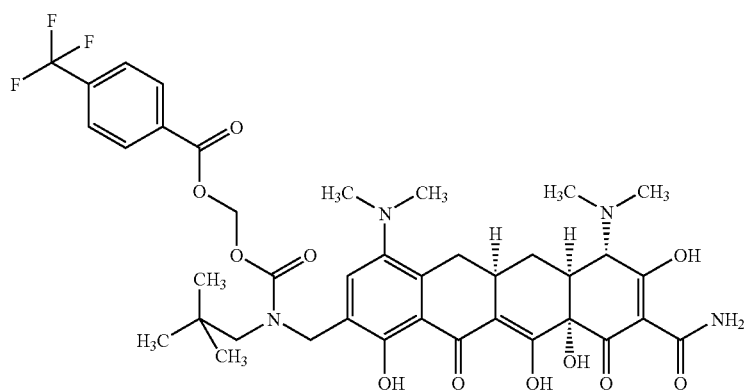
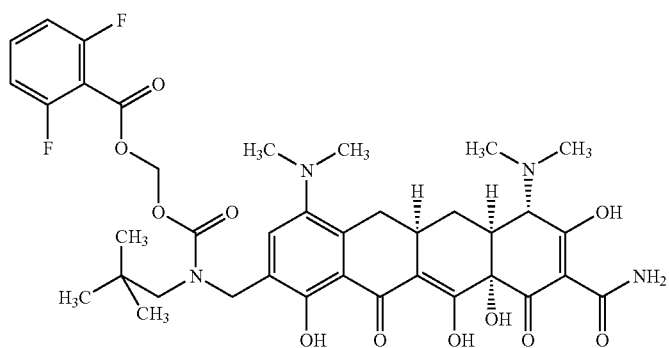

-continued
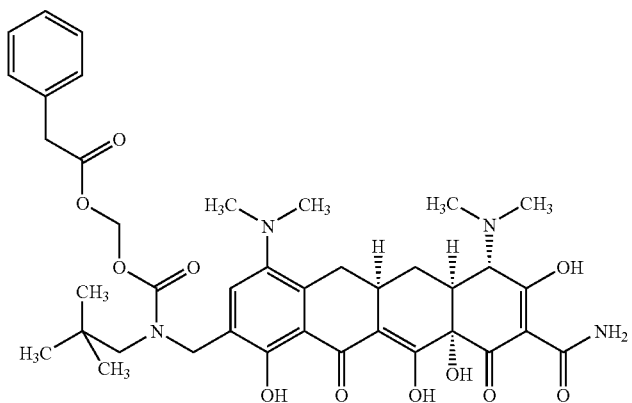
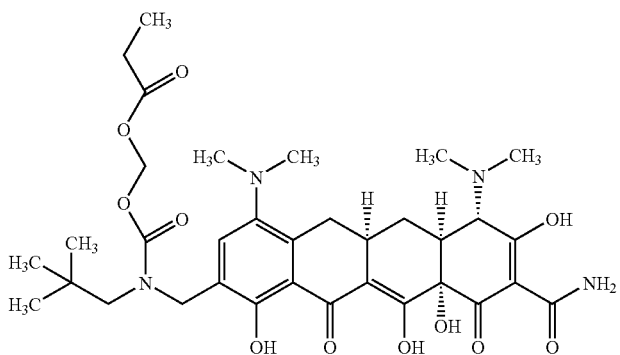
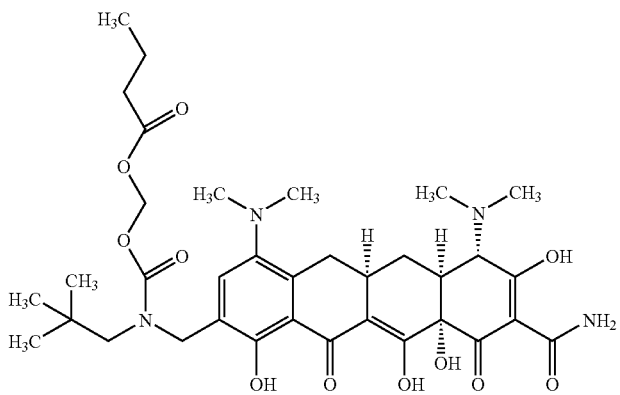
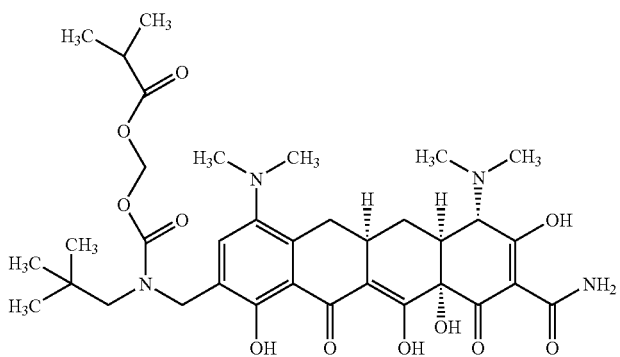

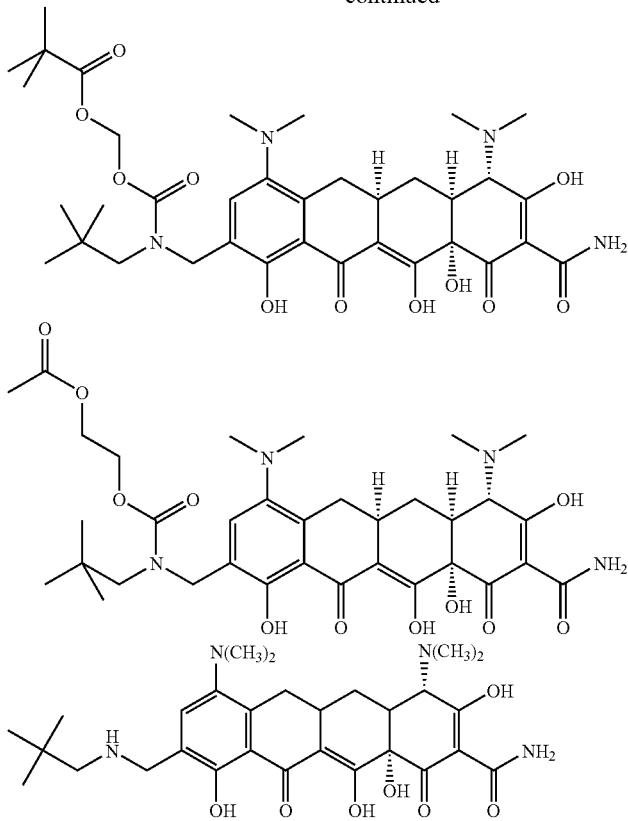

and pharmaceutically acceptable salts thereof.

The tetracycline compounds of this invention can be synthesized using the methods described in U.S. Ser. No. 10/877,454, U.S. Ser. No. 10/740,961, U.S. Pat. No. 6,846,939, U.S. Pat. No. 6,818,635, U.S. Pat. No. 6,683,068, and U.S. Ser. No. 10/337,914, the entire contents of each of which are incorporated herein by reference, and/or by other techniques known to those of ordinary skill in the art.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl(benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl(alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

In a further embodiment, the invention pertains to a kit comprising a tetracycline compound and instructions for administering a therapeutically effective amount of the tetracycline compound in combination with a bioavailability enhancing agent to the intestinal tract of a subject.

In another embodiment, the invention pertains to pharmaceutical composition comprising a therapeutically effective amount of a tetracycline compound in combination with a bioavailability enhancing agent and a pharmaceutically acceptable carrier for administration of said tetracycline compound to the intestinal tract. The bioavailability enhancing agent and the tetracycline compound may be administered concurrently in separate or in the same pharmaceutical composition.

The language "effective amount" of the tetracycline compound is that amount necessary or sufficient to treat a subject. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The language "pharmaceutically acceptable carrier" includes substances capable of being coadministered with the tetracycline compound(s), and which allow both to perform their intended function. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The tetracycline compounds of the invention and pharmaceutically acceptable salts thereof can be administered orally. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, aqueous suspensions, injectable solutions and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. The compositions of the invention may be formulated such that the tetracycline compositions are released over a period of time after administration.

For enteral application, particularly suitable are tablets, dragees or capsules having talc and/or carbohydrate carrier binder or the like, the carrier preferably being lactose and/or corn starch and/or potato starch. Sustained release compositions can be formulated including those wherein the active component is protected with differentially degradable coatings, e.g., by microencapsulation, multiple coatings, etc.

Enteric coatings (which generally do not substantially dissolve in solutions with a pH lower than about 5.5) may delay release of the tetracycline compound until delivery to the intestinal tract. Examples of enteric coatings include, but are not limited to, coatings made from methacrylic acid copolymers, cellulose acetate (and its succinate and phthalate versions), styrol maleic acid copolymers, polymethacrylic acid/acrylic acid copolymer, hydroxypropyl methyl cellulose phthalate, polyvinyl acetate phthalate, hydroxyethyl ethyl cellulose phthalate, hydroxypropyl methyl cellulose acetate succinate, cellulose acetate tetrahydrophtalate, acrylic resin, timellitate, and shellac, and combinations thereof.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats.

It will be appreciated that the actual preferred amounts of active compounds used in a given therapy will vary according to the specific compound being used, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

EXEMPLIFICATION OF THE INVENTION

Example 1

Bioavailability of 9-[(2,2, Dimethyl-propyl amino)-methyl]-Minocycline Following Intravenous Administration in Rats The bioavailability of 9-[(2,2, dimethyl-propyl amino)-methyl]-minocycline following intravenous administration in rats was studied. The freebase ("FB") and the HCl salt ("HCl salt") of 9-[(2,2, dimethyl-propyl amino)-methyl]-minocycline were used. All formulations were prepared fresh on the day of the experiment. Samples for pharmacokinetic analysis were collected from a cannula within the carotid artery of the rats. Intravenous doses of (1 mg/kg) were administered to rats through cannulas in either the jugular or portal veins. The results of this studied are summarized in Table 2.

TABLE 2

PK parameters following intravenous administration of 9-[(2,2, dimethyl-propyl amino)-methyl]-minocycline in rats.

| Formulation | Route of admin. | Fed state | AUC (ug*hr/mL) |
|---|---|---|---|
| FB | Jugular vein | Fasted | 0.57 (0.50; 0.63) |
| HCl salt | Jugular vein | Fed | 0.46 ± 0.04 |
| HCl salt | Jugular vein | Fasted | 0.59 (0.45; 0.73) |
| HCl salt | Portal vein | Fasted | 0.59 (0.52: 0.66) |

It was found that there were no significant differences in pharmacokinetic parameters after IV administration of the freebase (FB) or the HCl salt in fasted animals. However, tendency for higher clearance (~22%) was observed in a fed group. The total exposure (e.g., the area under the curve (AUC)) and clearance after administration of the HCL salt into the portal vein was equal to its exposure and clearance after administration into the jugular vein in fasted animals. It was determined that there were no significant effects of first pass hepatic elimination on pharmacokinetics of PTK after IV dosing.

Example 2

Bioavailability of 9-[(2,2, Dimethyl-propyl amino)-methyl]-Minocycline Following Oral Administration in Rats Solutions of 9-[(2,2, dimethyl-propyl amino)-methyl]-minocycline freebase (5 mg/kg [2 ml/kg]) were administered by oral gavage. The solutions were composed of 9-[(2,2, dimethyl-propyl amino)-methyl]-minocycline alone or in combination with bioavailability enhancing agents to assess their effect on oral bioavailability.

TABLE 3

Pharmacokinetic parameters of 9-[(2,2, dimethyl-propyl amino)-methyl[-minocycline following dosing via oral gavage.

| Formulation | AUC (hr*ug/mL) | % F [a] |
|---|---|---|
| FB, Polysorbate 80 (TWEEN-80) 10% | 0.47 | 16.6 (17.8; 15.3) |
| FB, Octanol | 0.26 | 9.3 (3.1: 15.4) |
| FB, Octanol:oil (1:9) | 0.15 ± 0.10 | 5.3 ± 3.5 |

TABLE 3-continued

Pharmacokinetic parameters of 9-[(2,2,
dimethyl-propyl amino)-methyl[-minocycline
following dosing via oral gavage.

| Formulation | AUC (hr*ug/mL) | % F [a] |
|---|---|---|
| FB, Ethanol:oil (1:9) | 0.20 ± 0.17 | 7.1 ± 6.2 |
| FB | 0.33 ± 0.12 | 11.7 ± 4.1 |
| FB, PTK-FB, NaBisulfite | 0.33 ± 0.12 | 11.7 ± 4.3 |
| FB, CaCl$_2$ | 0.24 ± 0.06 | 8.5 ± 2.0 |

The oral bioavailability (% F) for the various solutions is shown in Table 3. The % F was calculated using the IV data presented in Example 1 and the equation: % F=Oral AUC/IV AUC.

Example 3

Site of Absorption Effects of 9-[(2,2, Dimethyl-propyl amino)-methyl]-Minocycline in Rats In order to measure the effect of delivering 9-[(2,2, dimethyl-propyl amino)-methyl]-minocycline directly into the duodenum, rats bearing duodenal cannulas were administered 9-[(2,2, dimethyl-propyl amino)-methyl]-minocycline freebase alone or in combination with bioavailability enhancing agents to assess their effects on bioavailability.

TABLE 4

PK parameters of 9-[(2,2, dimethyl-propyl amino)-methyl]-minocycline following intra-duodenal administration.

| Formulation | AUC (ug*hr/mL) | % F |
|---|---|---|
| FB | 0.44 ± 0.15 | 15.4 ± 5.2 |
| FB, 10% Polysorbate 80 (TWEEN 80) | 0.79 (0.76; 0.82) | 28 (27; 29) |
| FB, 20% Polysorbate 80 (TWEEN 80) | 1.21 ± 0.18 | 42.7 ± 6.5 |
| FB, NaBis, Lubricant | 1.12 (1.18: 1.06) | 39.6 (41.6; 37.3) |
| FB, 0.5 mM EDTA | 0.89 ± 0.30 | 31.4 ± 10.7 |
| FB, 0.5 mM EDTA, 10% Polysorbate 80 (TWEEN 80) | 1.47 (1.79: 1.16) | 52.1 (63.3; 40.9) |

This study shows that there is a significant increase in AUC, when the freebase is administered directly to the rats' duodenum. It was also found that polysorbate 80 (TWEEN-80) had a positive effect on bioavailability (% F). Based on AUC, 10% and 20% polysorbate 80 (TWEEN-80) resulted in a 2-fold and 3-fold greater exposure, respectively. The increase in bioavailability was linearly related to the concentration of polysorbate 80 (TWEEN-80). It was also noted that 0.5 M of EDTA had a significant (2-fold) impact on bioavailability of the compound. The addition of both 0.5 M of EDTA and 10% polysorbate 80 (TWEEN-80) had a synergistic effect. Individually, each additive increased bioavailability by ~2-fold whereas both agents together had a greater than 3-fold effect. In addition, sodium bisulfite (an antioxidant) and colloidal silicon dioxide (AEROSIL) (a lubricant) also lead to a 2-fold increase in bioavailability.

Example 4

Effects of Permeability Enhancers on the Bioavailability of 9-[(2,2, Dimethyl-propyl amino)-methyl]-Minocycline As a control, a solution of 9-[(2,2, dimethyl-propyl amino)-methyl]-minocycline freebase ("freebase") was prepared using sterile water and the final pH was adjusted to ~5. To prepare the sodium caprate (sodium decanoate, a compound that increases paracellular permeability) containing solution, the freebase was first dissolved in sterile water and sodium caprate was then added to a final concentration of 13 mM. The resulting solution was administered to rats via oral gavage without pH adjustment. The solution of freebase containing 1.5% chitosan was then prepared by first dissolving the freebase in sterile water and then adjusting the pH of this solution (pH ~8.1) to a final pH ~5 using 1N HCl. Chitosan was then added to a final concentration of 1.5% and the resulting solution was administered to rats via oral gavage as a slurry.

TABLE 5

Effects of permeability enhancers on the bioavailability
of 9-[(2,2, dimethyl-propyl amino)-methyl]-minocycline
administered by oral gavage.

| Formulation | AUC (ug*hr/mL) | % F |
|---|---|---|
| FB (pH 8.1) | 0.33 ± 0.12 | 11.7 ± 4.1 |
| FB (pH 5) | 0.42 ± 0.11 | 14.7 ± 3.8 |
| FB, sodium caprate | 0.44 (0.37: 0.51) | 15.5 (13.1; 17.9) |
| FB, chitosan | 0.47 ± 0.25 | 16.6 ± 8.9 |

It was found that the permeability enhancers sodium caprate and chitosan did not show a statistically significant effect on bioavailability.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method for increasing oral bioavailability of a tetracycline compound in a subject, comprising administering said tetracycline compound to said subject in combination with a bioavailability enhancing agent such that said tetracycline compound is released in the intestinal tract, wherein said bioavailability enhancing agent is selected from ethylenediaminetetraacetic acid (EDTA) and sodium bisulfite, and wherein said tetracycline compound is

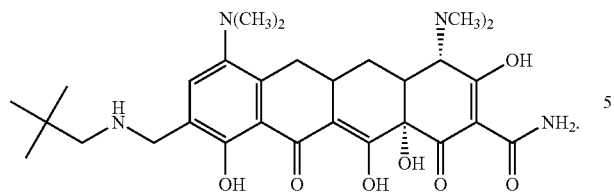

2. The method of claim 1, wherein the bioavailability is increased by about 5% or greater.

3. The method of claim 1, wherein the bioavailability is increased by about 10% or greater.

4. The method of claim 1, wherein the bioavailability is increased by about 25% or greater.

5. The method of claim 1, wherein the bioavailability is increased by about 40% or greater.

6. The method of claim 1, wherein the bioavailability is increased by about 50% or greater.

7. The method of claim 1, wherein said tetracycline compound is administered to the small intestine.

8. The method of claim 1, wherein said tetracycline compound is administered to the duodenum.

9. The method of claim 1, wherein said tetracycline compound is administered by a gastric feeding tube.

10. The method of claim 1, wherein said tetracycline compound is administered by a duodenal feeding tube.

11. The method of claim 1, wherein said tetracycline compound is formulated with an enteric coating.

12. The method of claim 1, wherein the bioavailability is increased by about 10%.

* * * * *